US010245346B2

(12) United States Patent
Locke et al.

(10) Patent No.: US 10,245,346 B2
(45) Date of Patent: Apr. 2, 2019

(54) ION EXCHANGE ABSORBENT SYSTEMS, APPARATUSES, AND METHODS

(71) Applicant: KCI Licensing, Inc., San Antonio, TX (US)

(72) Inventors: Christopher Brian Locke, Bournemouth (GB); Brian Andrews, Wimborne (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 507 days.

(21) Appl. No.: 14/869,649

(22) Filed: Sep. 29, 2015

(65) Prior Publication Data

US 2016/0095951 A1    Apr. 7, 2016

Related U.S. Application Data

(60) Provisional application No. 62/060,098, filed on Oct. 6, 2014, provisional application No. 62/096,669, filed on Dec. 24, 2014.

(51) Int. Cl.
*A61F 13/00* (2006.01)
*A61L 15/22* (2006.01)
(Continued)

(52) U.S. Cl.
CPC ........ *A61L 15/18* (2013.01); *A61F 13/00068* (2013.01); *A61F 13/00987* (2013.01);
(Continued)

(58) Field of Classification Search
CPC .......... A61F 13/00063; A61F 13/00068; A61F 13/00987; A61F 13/00991; A61F 13/022;
(Continued)

(56) References Cited

U.S. PATENT DOCUMENTS

| 1,355,846 A | 10/1920 | Rannells |
| 2,547,758 A | 4/1951 | Kelling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion corresponding to PCT Application No. PCT/US2015/053018 dated Nov. 17, 2015.
(Continued)

*Primary Examiner* — Adam Marcetich

(57) ABSTRACT

Systems, methods, and apparatuses for increasing liquid absorption are described. Some embodiments may include a dressing having an absorbent layer containing super-absorbent material as well as ionic-exchange media (IEM). In some embodiments, the absorbent layer may include absorbent fibers. The absorbent fibers may each include a super-absorbent core surrounded by a water-permeable layer onto which ionic-exchange media (IEM) may be grafted. As liquid comes into contact with the IEM, its ionic nature may be reduced, therefore protecting the absorbent qualities of the super-absorbent material.

21 Claims, 3 Drawing Sheets

(51) Int. Cl.

| | | |
|---|---|---|
| *A61L 15/42* | (2006.01) | |
| *A61L 15/60* | (2006.01) | |
| *A61L 15/18* | (2006.01) | |
| *A61M 1/00* | (2006.01) | |
| *G05B 19/418* | (2006.01) | |
| *A61L 15/26* | (2006.01) | |
| *A61L 15/44* | (2006.01) | |
| *A61L 15/24* | (2006.01) | |
| *A61L 15/28* | (2006.01) | |
| *A61F 13/02* | (2006.01) | |

(52) U.S. Cl.
CPC ...... *A61F 13/00991* (2013.01); *A61F 13/022* (2013.01); *A61F 13/0276* (2013.01); *A61L 15/22* (2013.01); *A61L 15/225* (2013.01); *A61L 15/24* (2013.01); *A61L 15/26* (2013.01); *A61L 15/28* (2013.01); *A61L 15/425* (2013.01); *A61L 15/44* (2013.01); *A61L 15/60* (2013.01); *A61M 1/0001* (2013.01); *A61M 1/0088* (2013.01); *G05B 19/41865* (2013.01); *A61F 2013/00314* (2013.01); *A61L 2300/104* (2013.01); *A61L 2300/106* (2013.01); *A61L 2300/404* (2013.01); *A61L 2420/00* (2013.01)

(58) Field of Classification Search
CPC ....... A61F 13/0276; A61F 2013/00314; Y10T 442/609; D01D 5/30; D01D 5/32; D01D 5/34; D01D 5/36; A61M 1/0001; A61M 1/0088

See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,798,850 A | 7/1957 | Voigtman et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,287,153 A | 9/1981 | Towsend | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,818,598 A * | 4/1989 | Wong | A61L 15/28 428/326 |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,124,391 A * | 9/2000 | Sun | A61L 15/18 523/223 |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,528,157 B1 * | 3/2003 | Hussain | C09K 8/805 428/325 |
| 6,553,998 B2 | 4/2003 | Heaton et al. | |
| 6,610,898 B1 * | 8/2003 | Magnusson | A61F 13/53747 604/365 |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |

(56) References Cited

U.S. PATENT DOCUMENTS

| | | | |
|---|---|---|---|
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0040210 A1* | 4/2002 | Luccio | A61L 15/20 604/367 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0168912 A1* | 11/2002 | Bond | D01F 8/14 442/415 |
| 2002/0193030 A1* | 12/2002 | Yao | D01F 8/06 442/366 |
| 2003/0138631 A1* | 7/2003 | Mitchell | A61L 15/60 428/402.22 |
| 2005/0031850 A1* | 2/2005 | Mitchell | A61F 13/53 428/327 |
| 2005/0124799 A1* | 6/2005 | Pesce | A61L 15/28 536/20 |
| 2005/0130540 A1* | 6/2005 | Crane | D01D 5/082 442/364 |
| 2005/0194141 A1* | 9/2005 | Sinclair | C09K 8/805 166/280.2 |
| 2005/0247472 A1* | 11/2005 | Helfer | A61N 1/16 174/36 |
| 2007/0044903 A1 | 3/2007 | Wisneski et al. | |
| 2007/0250024 A1* | 10/2007 | Mitchell | A61F 13/15203 604/372 |
| 2008/0011674 A1* | 1/2008 | Nakagaki | B01D 39/1653 210/496 |
| 2008/0202539 A1* | 8/2008 | Banks | A24D 3/064 131/332 |
| 2010/0003517 A1* | 1/2010 | Hansson | A61F 13/53 428/373 |
| 2010/0323945 A1* | 12/2010 | Simonsen | C11D 3/222 510/360 |
| 2011/0082105 A1* | 4/2011 | Fevola | A61K 8/4973 514/58 |
| 2012/0055643 A1* | 3/2012 | Neal | C11D 17/041 162/164.6 |
| 2013/0096524 A1 | 4/2013 | Riesinger | |
| 2014/0026910 A1* | 1/2014 | Bundren | B29C 47/12 131/332 |
| 2014/0138305 A1* | 5/2014 | Crandall | B24B 37/245 210/502.1 |
| 2014/0163491 A1 | 6/2014 | Schuessler et al. | |
| 2014/0200532 A1 | 7/2014 | Robinson et al. | |
| 2014/0249495 A1 | 9/2014 | Mumby et al. | |
| 2015/0080788 A1 | 3/2015 | Blott et al. | |
| 2016/0222548 A1* | 8/2016 | Agboh | B29C 47/0014 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2005051461 A1 | 6/2005 |
| WO | 2009157877 A1 | 12/2009 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

(56) References Cited

OTHER PUBLICATIONS

Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?, Radak, and P. Peška, "Vacuum Therapy in the Treatment of Peripheral Blood Vessels," Timok Medical Journal 11 (1986), pp. 161-164 (certified translation).
F.E. E Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: a Reference Source for Clinicians; Jul. 2007.
Louis C. Argenta, MD and Michael J. Morykwas, PHD; Vacuum-Assisted Closure: A New Method for Wound control and Treatment: Clinical Experience; Annals of Plastic Surgery; vol. 38, No. 6, Jun. 1997; pp. 563-576.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
James Economy et al: "Polymeric Ion-Exchange Fibers", Industrial & Engineering Chemistry Research, vol. 41, No. 25, Dec. 1, 2002, pp. 6436-6442.
Extended European Search Report for Corresponding Application No. 181935628, dated Jan. 4, 2019.

* cited by examiner

ION EXCHANGE ABSORBENT SYSTEMS, APPARATUSES, AND METHODS

This application claims priority to and the benefit of U.S. Provisional Patent Application No. 62/060,098, filed Oct. 6, 2014, entitled "Multi-Function Dressing Structure for Negative Pressure Therapy," to Robinson et al., and U.S. Provisional Patent Application No. 62/096,669, filed Dec. 24, 2014, entitled "Ion Exchange Absorbent Systems, Apparatuses, and Methods, to Locke et al., both of which are hereby incorporated by reference.

TECHNICAL FIELD

The invention set forth in the appended claims relates generally to treating tissue sites and processing fluids. More particularly, but not by way of limitation, the subject matter described herein relates to absorbents with ion-exchange media.

BACKGROUND

While the benefits of using absorbent materials in wound care are known, the cost and complexity of treating particular types of wounds can be a limiting factor, particularly when combined with negative-pressure therapy. In particular, wound dressings that incorporate absorbents formed of superabsorbent polymers often provide a practical absorption capacity that is less than the rated absorption capacity. This may necessitate the use of additional absorbent or increase the number of dressing changes needed to treat a tissue site. Increasing the amount of absorbent used and the number of dressing changes can negatively affect the efficacy and cost of wound care.

BRIEF SUMMARY

According to an illustrative embodiment, a fiber may include an absorbent core, a filter layer, and an ion-exchange media. The filter layer may be disposed around the absorbent core. The ion-exchange media may be disposed in the filter layer and adapted to reduce an ionic concentration of a fluid.

According to another illustrative embodiment, an absorbent dressing for treating a tissue site may include an ion-exchange media and an absorbent. The ion-exchange media may be adapted to reduce an ionic concentration of the fluid. The absorbent material may be adapted to absorb fluid from the tissue site.

According to yet another illustrative embodiment, a system for treating a tissue site may include a reduced-pressure source, an absorbent layer, and a drape. The reduced-pressure source may be for providing reduced pressure. The absorbent layer may be adapted to be in fluid communication with the reduced-pressure source. The absorbent layer may include an absorbent material adapted to absorb fluid from the tissue site, and an ion-exchange media adapted to reduce an ionic concentration of the fluid. The drape may be adapted to cover the absorbent layer.

According to still another illustrative embodiment, a container for storing fluids from a tissue site may include a body and an absorbent layer. The body may include an interior portion, a fluid inlet, and a fluid outlet. The absorbent layer may include an absorbent material and an ion-exchange media adapted to reduce an ionic concentration of fluid in the interior portion.

According to still another illustrative embodiment, a method for treating a tissue site may include disposing an absorbent layer proximate to the tissue site and attaching the absorbent layer to the tissue site with a drape. The absorbent layer may include an absorbent material and an ion-exchange media adapted to reduce an ionic concentration of a fluid drawn into the absorbent layer. The method may also include disposing a manifold between the tissue site and the absorbent layer, fluidly coupling a reduced-pressure source to the manifold, and supplying reduced pressure to the tissue site to draw fluid from the tissue site to the absorbent layer.

According to still another illustrative embodiment, a system for treating a tissue site may include a reduced-pressure source, a fluid storage member, a manifold, a drape, and an absorbent layer. The fluid storage member may be adapted to be in fluid communication with the tissue site and the reduced-pressure source. The manifold may be adapted to receive reduced pressure and distribute the reduced pressure to the tissue site. The drape may be adapted to cover the manifold and provide a substantially fluid-tight seal at the tissue site. The absorbent layer may include a carrier material and a plurality of multi-layer fibers. Each multi-layer fiber may include an ion-exchange media disposed around an absorbent core.

Other aspects, features, and advantages of the illustrative embodiments will become apparent with reference to the drawings and detailed description that follow.

DESCRIPTION OF EXAMPLE EMBODIMENTS

In the following detailed description of non-limiting, illustrative embodiments, reference is made to the accompanying drawings that form a part hereof. Other embodiments may be utilized, and logical, structural, mechanical, electrical, and chemical changes may be made without departing from the scope of the appended claims. To avoid detail not necessary to enable those skilled in the art to practice the embodiments described herein, the description may omit certain information known to those skilled in the art. The following detailed description is non-limiting, and the scope of the illustrative embodiments are defined by the appended claims.

Figure 1:
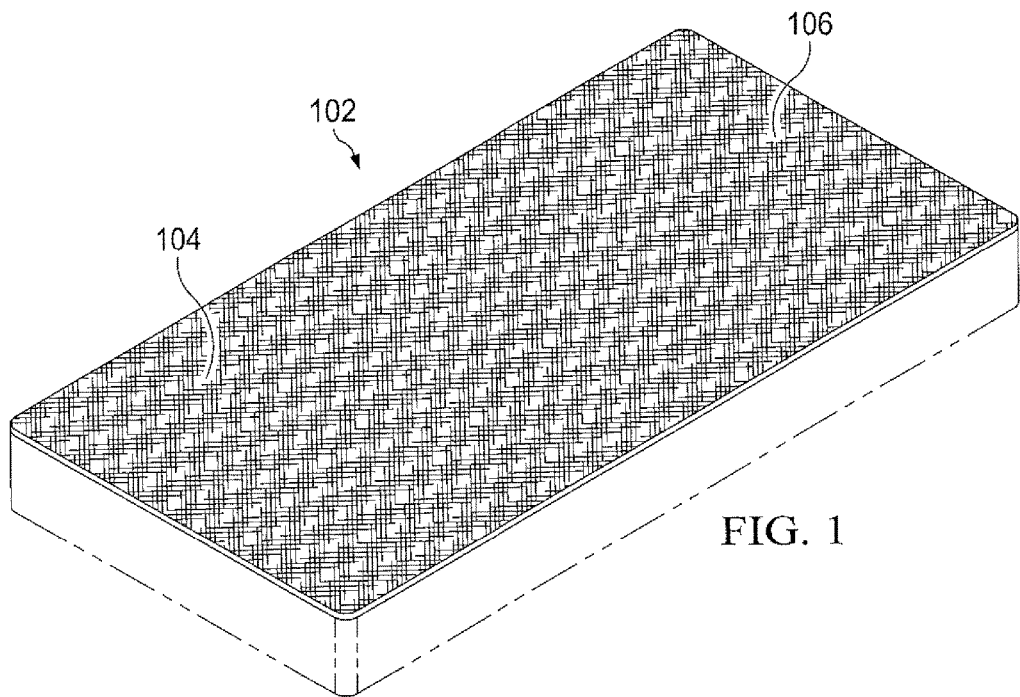
FIG. 1 is a schematic diagram of an illustrative embodiment of an absorbent layer.

FIG. 1 is a schematic diagram of an exemplary embodiment of an absorbent layer 102. The absorbent layer 102 may include or consist of a woven or non-woven matrix, such as a fiber matrix 104. The fiber matrix 104 may be formed from long fibers, such as fibers 106, which may be bundled or twisted together. The fiber matrix 104 may include the fibers 106 arranged along both the length and width of the absorbent layer 102. The absorbent layer 102 may include more than one layer of the fiber matrix 104. For example, in some embodiments, the number of layers of fiber matrices 104 can be tailored to a particular type of wound or tissue site and the amount of fluid or exudates expected to be released from the wound.

Figure 2:
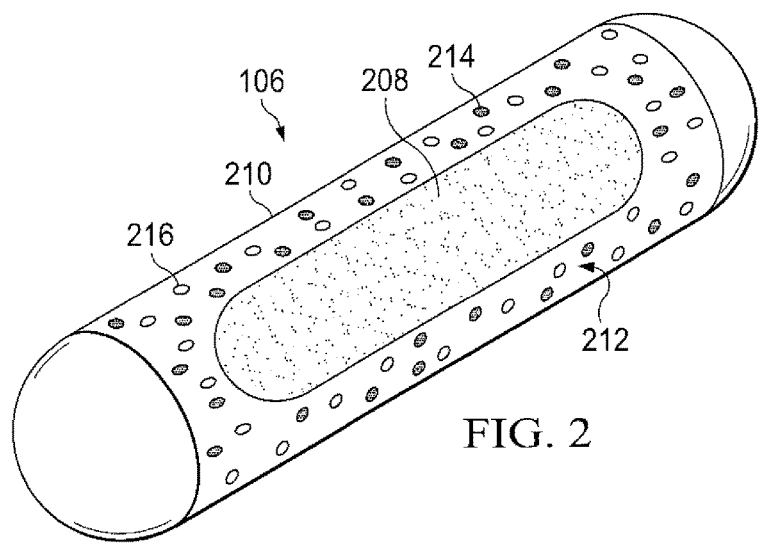
FIG. 2 is a sectional schematic diagram of an absorbent fiber of the absorbent layer of FIG. 1.

FIG. 2 is a sectional schematic diagram of an example embodiment of the fiber 106, illustrating additional details that may be associated with some embodiments. The fiber 106 may include multiple layers. For example, in the embodiment of FIG. 2, the fiber 106 may include an absorbent core, such as a core 208, and a filter layer 210.

The core 208 may include or consist of an absorbent material, which may be a material used to hold, stabilize, and/or solidify liquids. The absorbent material may be a hydrophilic material. The absorbent material may provide an absorption gradient to draw or otherwise wick fluid away from the tissue site. Fluid from the tissue site may be drawn by the absorption gradient and then absorbed by the absorbent material. The absorbent material may retain or bond to the fluid in conjunction with a physical or chemical change to the absorbent material. The absorbent material may, for example, gel, increase in viscosity, or otherwise thicken upon contact with fluid from the tissue site, thereby trapping the fluid. The wicking properties of the absorbent material may help to quickly draw fluid, e.g. exudate, away from the tissue site, and thus may prevent the accumulation of fluid at or near the tissue site.

In some embodiments, the absorbent material may comprise a super-absorbent material. For example, the absorbent material may comprise one or more super-absorbent materials, such as, carboxymethyl cellulose (CMC), or a carboxymethylcellulose salt, a cross-linked hydrophilic acrylic, or a cross-linked hydrophilic acrylic salt, or an acrylamide. In some embodiments, for example, the super-absorbent material may be a super-absorbent polymer (SAP), such as the type commonly referred to as a hydrogel or a hydrocolloid. Generally, relative to their mass, a SAP can absorb and retain large quantities of liquid, and in particular, water. Medical disposables, such as canisters and dressings, can use a SAP to retain and stabilize or solidify wound fluids and other exudate.

A SAP may be formed in several ways, for example, by gel polymerization, solution polymerization, or suspension polymerization. Gel polymerization may involve blending of acrylic acid, water, cross-linking agents, and ultraviolet (UV) initiator chemicals. The blended mixture may be placed into a reactor where the mixture is exposed to UV light to cause crosslinking reactions that form the SAP. The mixture may be dried and shredded before subsequent packaging and/or distribution. Solution polymerization may involve a water-based monomer solution that produces a mass of reactant polymerized gel. The monomer solution may undergo an exothermic reaction that drives the cross-linking of the monomers. Following the cross-linking process, the reactant polymer gel may be chopped, dried, and ground to its final granule size. Suspension polymerization may involve a water-based reactant suspended in a hydrocarbon-based solvent.

In general, SAPs can absorb liquids by bonding with water molecules through hydrogen bonding. Hydrogen bonding involves the interaction of a polar hydrogen atom with an electronegative atom. As a result, SAPs can absorb water based on the ability of the hydrogen atoms in each water molecule to bond with the hydrophilic polymers of the SAP having electronegative ionic components. High-absorbing SAPs can be formed from ionic cross-linked hydrophilic polymers such as acrylics and acrylamides in the form of salts or free acids.

Because SAPs are ionic, they can be affected by the soluble ionic components within a solution being absorbed and may, for example, absorb less saline than pure water. The lower absorption rate of saline is caused by the sodium and chloride ions blocking some of the water absorbing sites on a SAP. If fluid absorbed by a SAP is a solution containing dissolved mineral ions, fewer hydrogen atoms of the water molecules in the solution may be free to bond with the SAP. Thus, the ability of a SAP to absorb and retain fluid may be dependent upon the ionic concentration of the fluid. For example, a SAP may absorb and retain de-ionized water up to 500 times the weight of the dry SAP. In volumetric terms, a SAP may absorb fluid volumes as high as 30 to 60 times the dry volume of the SAP. Other fluids having a higher ionic concentration may be absorbed at lower quantities. For example, a SAP may only absorb and retain a solution that is 0.9% salt (NaCl) up to 50 times the weight of the dry SAP.

Since wound fluids may contain salts, such as sodium, potassium, and calcium, the absorption capacity of a SAP may be significantly reduced when used in wound treatment applications. The reduction in absorption capacity may necessitate using additional quantities of a SAP that can significantly add to the overall bulkiness of the dressing or fluid storage device. Additionally, in many therapy systems, using additional quantities of a SAP may not be possible due to size limitations of the dressing or container.

The systems, apparatuses, and methods described herein can overcome these shortcomings and others by providing absorbent fibers with ionic-exchange media (IEM). Thus, a simplified design for removing ionic material from wound fluid media combined with super-absorbing functionality is provided. Such a design can be incorporated as part of a wound dressing, a fluid-handling canister, or a storage container.

Referring still to FIG. 2, for example, the core 208 may be at least partially enclosed within the filter layer 210, and an TEM 212 may be disposed within the filter layer 210. In some embodiments, the filter layer 210 may be coated onto the outside of the core 208, and may be a water-soluble or water-swelling polymer. Water-soluble or water-swelling polymers may include cross-linked polyvinyl alcohol, polyvinyl pyrrolidone, polyurethane, polyacrylamide, and polyethylene oxide. The TEM 212 may be ion-exchange resins in the form of beads or other particles, which may be grafted onto the surface of the filter layer 210. Alternatively, the ion-exchange resins may be grafted onto polystyrene and dispersed throughout the filter layer 210. The diameter of the fiber 106 may be in the range of about 1-50 microns, and more typically in the range of about 5-25 microns, depending on the dimensions of the core 208 and filter layer 210 that may be desired or appropriate for a particular application.

The IEM 212 may reduce the number of ionized particles within the wound fluid coming into contact with the core 208. For example, the TEM 212 may provide a reduction of the number of ionized particles within the wound fluid somewhere in the range of 1%-80%. In some preferred embodiments, the IEM 212 may provide an approximately 25% reduction in ionized particle concentration within the wound fluid. The IEM 212 may be adapted to provide an exchange of ions between two electrolytes, or between an electrolyte solution and a complex. An electrolyte is a compound that ionizes when dissolved in a suitable ionizing solvent, such as water. An electrolyte solution may contain a dissolved salt, such as NaCl. A complex may be an atom or ion having a surrounding array of bound molecules or anions known as ligands or complexing agents. IEM can replace cations and anions in an electrolyte or an electrolyte solution as the electrolyte or electrolyte solution interacts with the IEM. Cations are ions having a net positive charge, for example, Na+. Cations may be replaced in the electrolyte or electrolyte solution with hydrogen (H+) ions of the TEM. Anions are ions having a net negative charge, for example, Cl−. Anions may be replaced in the electrolyte or electrolyte solution with hydroxyl (OH−) ions of the IEM. The H+ and OH− ions may combine in the electrolyte or electrolyte solution to form water.

In some embodiments, the IEM 212 may be porous beads formed from cross-linked polymers, such as polystyrene, that are doped or grafted with acidic polymers. An example of an acidic polymer may include poly(2-acrylamido-2-methyl-1-propanesulfonic acid) or polyAMPS. The polyAMPS can exchange positively charged salt ions for H+. An example of an alkaline polymer may include poly (acrylamido-N-propyltrimethylammonium chloride) or polyAPTAC. The polyAPTAC exchange negatively charged salt ions for OH—.

The IEM 212 of the filter layer 210 may also include a mixture of both cation-exchange media 214 and anion-exchange media 216 to form a mixed bed ion-exchange media that can simultaneously absorb both anions and cations. Non-limiting examples of the mixed bed media include AMBERLITE IRN150 and TMD-8. The IEM may be formed of ion-exchange resins, zeolites, montmorillonite, bentonites, clay, or soil humus, for example. Ion-exchange resins, also known as ion-exchange polymers, are insoluble matrices normally in the form of small beads fabricated from an organic polymer substrate. Ion-exchange resins may have pores on the surface that trap and release ions. Ion-exchange resins can include cross-linked polystyrene, for example. Zeolites are microporous, aluminosilicate minerals. Zeolites have a porous structure that allow cations, such as Na+, K+, Ca2+, and Mg2+, for example, to be accommodated by the zeolite. Common zeolites include analcime, chabazite, clinoptilolite, heulandite, natrolite, phillipsite, and stilbite, for example. In addition to the above materials, other ion-exchange media include activated charcoal, both particulate and in the form of fabrics or non-wovens, for example, and Zorflex, also known as Chemviron Carbon. Chemviron Carbon may also be known as 100% activated carbon.

The core 208 may be in the form of a super-absorbent fiber, such as one made from an alginate or particles fused together, for example, carboxymethyl cellulose (CMC) or polyacrylic acid. In some embodiments, super-absorbent fibers may be formed or manufactured by various spinning processes, such as, but not limited to, wet spinning, dry spinning, melt spinning, gel spinning, or electro-spinning. As a first step in the process, the fiber-forming polymer may be converted into a fluid state. The polymer can be melted, dissolved in a solvent, or chemically treated to form a soluble derivative. The molten polymer may be extruded through a spinneret, a multi-pored device, to form fibers.

In some embodiments, the fibers 106 may be formed by simultaneously extruding the super-absorbent core material and the filter layer material containing the ion-exchange media using a co-extrusion process. For example, in some embodiments, the co-extrusion process involves the use of an extruder to create the outer filter layer material, which may contain the ion-exchange media, and an auxiliary system for injecting or filling the outer filter layer material with the super-absorbent core material.

Figure 3:
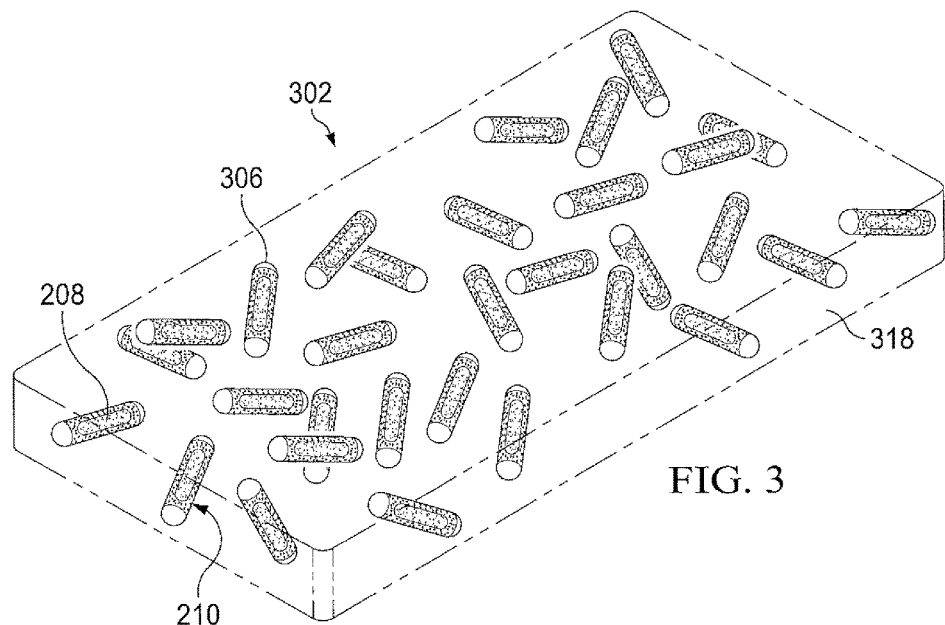
FIG. 3 is a schematic diagram of another illustrative embodiment of an absorbent layer.

Referring more specifically to FIG. 3, a schematic diagram illustrating another exemplary embodiment of a fiber matrix is shown. A fiber matrix 302 as illustrated in FIG. 3 may include short fibers 306 having characteristics similar or analogous to the fibers 106. For example, the fibers 306 may include a core, such as the core 208 encapsulated by an IEM layer, such as the filter layer 210. In some example embodiments, the fibers 306 may be dispersed in a carrier material, such as a carrier 318. The fibers 306 may have a variety of sizes or shapes, depending on a variety of factors, including the amount of liquids anticipated to be released by a tissue site, but preferably have a diameter in the range of about 1-50 microns, and more typically in the range of about 5-25 microns. In some embodiments, the carrier 318 may be a continuous polymer water-permeable matrix, perforated to permit transmission of negative pressure. Such polymers may include polymers and copolymers of polyvinyl alcohol, polyacrylic acid and its salts (sodium and potassium), carboxymethyl cellulose (CMC), other cellulosics, polyacrylamides, polyurethanes, and polyethylene oxides and glycols. In some embodiments, the carrier may also be a textile, formed from woven or non-woven fibers, for example, poly- and copoly-ester, polyolefin, cellulosics, or blends of any of these materials.

Figure 4:
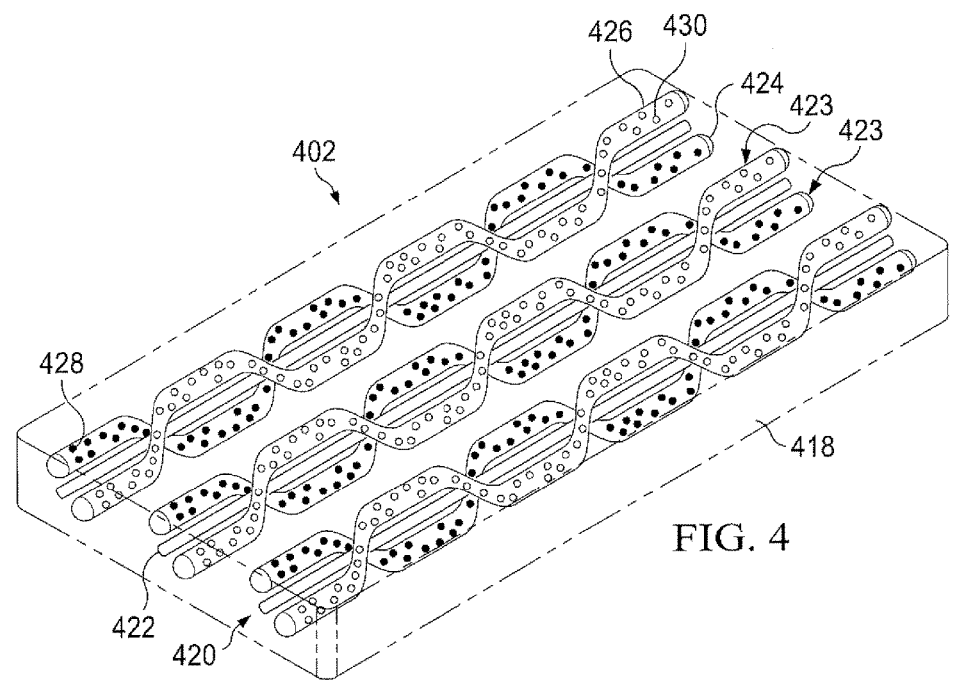
FIG. 4 is a schematic diagram of another illustrative embodiment of an absorbent layer.

FIG. 4 illustrates another exemplary embodiment of a fiber matrix. The fiber matrix 402 of FIG. 4 may include fibers 420, which may include multiple layers. For example, in the embodiment of FIG. 4, the fibers 420 may include an absorbent strand, such as a core 422 and filter strands 423 having IEM. In some embodiments, the core 422 may be may be in the form of a super-absorbent strand, and the filter strands may be twisted around the core 422. In some embodiments, fibers such as the fibers 420 may be dispersed in a carrier material, such as a carrier 418. The filter strands 423 may include acidic-exchange strands 424, which may include acidic-exchange media 428, and alkaline-exchange strands 426, which may include alkaline-exchange media 430. In some embodiments, the filter strands 423 may include cation-exchange resins or anion-exchange resins. In other embodiments, the filter strands 423 may include a combination of cation- and anion-exchange resins.

In the example embodiment of FIG. 4, the filter strands 423 can reduce or remove the ionic material from fluid before the fluid contacts the core 422. By including each of the three functional elements, namely a super-absorbent core, the acidic ion-exchange medium, and the alkaline ion-exchange medium, as separate strands, manufacturing of the fiber 420 can be simplified. For example, a fiber production or spinning method where four or more feed-stock streams are required to remain consistent with each other to produce a single multi-component fiber may not be needed.

Absorbent fibers with ion-exchange media, such as the fiber 106 or the fiber 420, may have many beneficial or advantageous applications. For example, an absorbent layer having absorbent fibers with ion-exchange media, such as the fiber matrix 104, the fiber matrix 302, or the fiber matrix 402, may be particularly advantageous for treating wounds with reduced pressure. Treatment of wounds or other tissue with reduced pressure may be commonly referred to as "reduced-pressure therapy," but is also known by other names, including "negative-pressure wound therapy," "negative-pressure therapy," "vacuum therapy," and "vacuum-assisted closure," for example. Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

Figure 5:
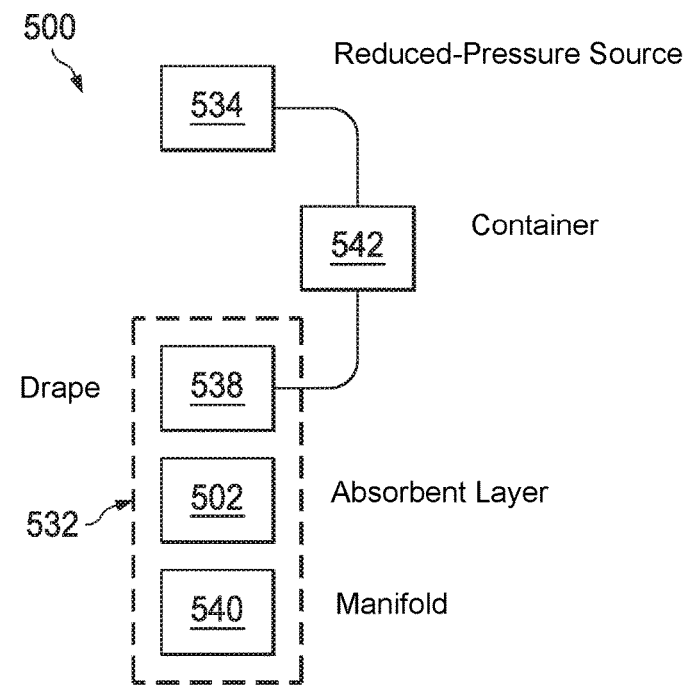
FIG. 5 is a functional block diagram illustrating a reduced-pressure therapy system that may be associated with some embodiments of an absorbent layer.

FIG. 5 is a schematic diagram of an example embodiment of a reduced-pressure therapy system 500 that may include absorbent fibers with an ion-exchange media. For example, the reduced-pressure therapy system 500 may include a dressing 532, which can be positioned proximate to a tissue site, and a reduced-pressure source 534 for providing reduced pressure to the dressing 532. In some embodiments, the dressing 532 may include a manifold 540, an absorbent layer 502, and a drape 538. The absorbent layer 502 may incorporate any combination, in whole or in part, of suitable features, structures, or elements of the fiber matrices or fibers with ion-exchange media described herein. For example, the absorbent layer 502 may incorporate the fiber matrix 104, the fiber matrix 302, the fiber matrix 402, or any suitable combination of features of these embodiments. The dressing 532 may be fluidly coupled to the reduced-pressure source 534. The reduced-pressure therapy system 500 may also include an exudate container, such as container 542, coupled to the dressing 532 and to the reduced-pressure source 534.

The term "tissue site" may refer to a wound or defect located on or within tissue, including without limitation, bone tissue, adipose tissue, muscle tissue, neural tissue, dermal tissue, vascular tissue, connective tissue, cartilage, tendons, or ligaments. A tissue site may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, reduced pressure may be used in certain tissue areas to grow additional tissue that may be harvested and transplanted to another tissue location.

A reduced-pressure source, such as the reduced-pressure source 534, may be a reservoir of air at a reduced pressure, or may be a manually or electrically-powered device that can reduce the pressure in a sealed volume, such as a vacuum pump, a suction pump, a wall suction port available at many healthcare facilities, or a micro-pump, for example. The reduced-pressure source may be housed within or used in conjunction with other components, such as sensors, processing units, alarm indicators, memory, databases, software, display devices, or user interfaces that further facilitate reduced-pressure therapy. While the amount and nature of reduced pressure applied to a tissue site may vary according to therapeutic requirements, the pressure may be a rough vacuum between about −5 mm Hg (−667 Pa) and about −500 mm Hg (−66.7 kPa). In some embodiments, the pressure may be between about −75 mm Hg (−9.9 kPa) and about −300 mm Hg (−39.9 kPa).

In general, exudates and other fluids may flow toward lower pressure along a fluid path. Further, fluids may be attracted to flow through permeable materials along a path of increasing hydrophilicity or absorbency among the materials. Thus, the term "downstream" may refer to components that are further along a fluid path than components that may be referred to as "upstream." Similarly, it may be convenient to describe certain features in terms of fluid "inlet" or "outlet" in such a frame of reference. This orientation is generally presumed for purposes of describing various features and components of negative-pressure therapy systems herein. However, the fluid path may also be reversed in some applications (such as by substituting a positive-pressure source for a negative-pressure source) and this descriptive convention should not be construed as a limiting convention.

"Reduced pressure" may refer to a pressure less than a local ambient pressure, such as the ambient pressure in a local environment external to a sealed therapeutic environment. The local ambient pressure may also be the atmospheric pressure at which a patient is located. Further, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The components of the reduced-pressure therapy system 500 may be coupled directly or indirectly. Components may be fluidly coupled to each other to provide a path for transferring fluids (for example, liquid and/or gas) between the components. In some exemplary embodiments, components may be fluidly coupled with conduits, such as tubes. A "tube," as used herein, may refer to a pipe, hose, conduit, or other elongated structure with one or more lumina adapted to convey fluids between two ends. In some exemplary embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

The manifold 540 may be adapted to be in fluid communication with a tissue site, the absorbent layer 502, and the drape 538. For example, the manifold 540 may be placed within, over, on, or otherwise proximate to a tissue site. The absorbent layer 502 may be placed between the tissue site or the manifold 540 and the drape 538. The drape 538 may be placed over the manifold 540 and the absorbent layer 502 and sealed to tissue proximate to the tissue site. The tissue proximate to the tissue site may be undamaged epidermis peripheral to the tissue site. Thus, the dressing 532 can provide a sealed therapeutic environment proximate to the tissue site, substantially isolating the tissue site from the external environment. The reduced-pressure source 534 can reduce pressure in the sealed therapeutic environment. Reduced pressure applied uniformly through the manifold 540 in the sealed therapeutic environment can induce macrostrain and microstrain in the tissue site, as well as remove exudates and other fluids from the tissue site.

In some embodiments, the manifold 540 may be adapted to contact a tissue site. The manifold 540 may be partially or fully in contact with a tissue site. If a tissue site extends into tissue from a tissue surface, for example, the manifold 540 may partially or completely fill the tissue site. In other exemplary embodiments, the manifold 540 may be placed over a tissue site. The manifold 540 may take many forms, and may have many sizes, shapes, or thicknesses depending on a variety of factors, such as the type of treatment being implemented or the nature and size of the tissue site. For example, the size and shape of the manifold 540 may be adapted to the contours of deep and irregular shaped tissue sites.

The manifold 540 may comprise a substance or structure adapted to distribute reduced pressure across a tissue site, remove fluids from across a tissue site, or both. In some exemplary embodiments, the manifold 540 may also facilitate delivering fluids across a tissue site, for example, if a fluid path is reversed or a secondary fluid path is provided. The manifold 540 may include flow channels or pathways that distribute fluids provided to and removed from a tissue site around the manifold 540. In one exemplary embodiment, the flow channels or pathways may be interconnected to improve distribution of fluids provided to or removed from a tissue site. For example, cellular foam, open-cell foam, porous tissue collections, and other porous material, such as gauze or felted mat may include structural elements arranged to form flow channels. Liquids, gels, and other foams may also include or be cured to include flow channels configured to distribute fluid across a tissue site.

In one exemplary embodiment, the manifold 540 may be a porous foam material having interconnected cells or pores adapted to distribute reduced pressure across a tissue site in a substantially uniform manner. The foam material may be either hydrophobic or hydrophilic. In one non-limiting example, the manifold 540 can be an open-cell, reticulated polyurethane foam such as GranuFoam® dressing available from Kinetic Concepts, Inc. of San Antonio, Tex.

In an example embodiment in which the manifold 540 may be made from a hydrophilic material, the manifold 540 may also wick fluid away from the tissue site, while continuing to distribute reduced pressure to the tissue site. The wicking properties of the manifold 540 may draw fluid away from the tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The manifold 540 may further promote granulation at the tissue site when pressure within the sealed therapeutic environment is reduced. For example, any or all of the surfaces of the manifold 540 may have an uneven, coarse, or jagged profile that can induce microstrains and stresses at the tissue site when reduced pressure is applied through the manifold 540 to a tissue site.

In one exemplary embodiment, the manifold 540 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The manifold 540 may further serve as a scaffold for new cell-growth, or a scaffold material may be used in conjunction with the manifold 540 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The drape 538 is an example of a sealing member. A sealing member may be constructed to provide a fluid seal between two components or two environments, such as between a therapeutic environment and a local external environment. The sealing member may be, for example, an impermeable or semi-permeable, elastomeric film that can provide a seal adequate to maintain a reduced pressure at a tissue site for a given reduced-pressure source. For semi-permeable materials, the permeability generally should be low enough that a desired reduced pressure may be maintained. An attachment device may be used to attach a sealing member to an attachment surface, such as undamaged epidermis, a gasket, or another sealing member. The attachment device may take many forms. For example, an attachment device may be a medically-acceptable, pressure-sensitive adhesive that extends about a periphery, a portion of, or an entirety of the sealing member. Other exemplary embodiments of an attachment device may include a double-sided tape, paste, hydrocolloid, hydrogel, silicone gel, organogel, or an acrylic adhesive.

In some embodiments, the reduced pressure developed by the reduced-pressure source 534 may be delivered through a tube to a connector. The connector may be a device configured to fluidly couple the reduced-pressure source 534 to the sealed therapeutic environment formed by the drape 538. In some embodiments, the connector may include a flange portion that couples to the drape 538 and a port portion that fluidly couples to the tube. In one exemplary embodiment, the connector may be a T.R.A.C.® Pad or Sensa T.R.A.C.® Pad available from Kinetic Concepts, Inc. of San Antonio, Tex. In other exemplary embodiments, the connector may also be a conduit inserted through the drape 538. The connector allows the reduced pressure to be delivered to the sealed therapeutic environment between the drape 538 and the tissue site. In some embodiments, the connector may extend through the drape 538 to the absorbent layer 502, but numerous arrangements are contemplated. The connector can deliver the reduced pressure through the drape 538 of the dressing 532 to the manifold 540.

The absorbent layer 502 is also preferably permeable to gases. For example, in some embodiments, the absorbent layer 502 may include fibers 106, in which the core 208 may comprise a SAP. Reduced pressure may be transferred with and through spaces or voids between the fibers 106 in such embodiments of the absorbent layer 502.

The container 542 is representative of a container, canister, pouch, or other storage component that can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with reduced-pressure therapy. Some exemplary embodiments of the reduced-pressure therapy system 500 may not include the container 542; instead, these exemplary embodiments of the therapy system 500 handle fluid storage with the dressing 532 and the absorbent layer 502.

Figure 6:
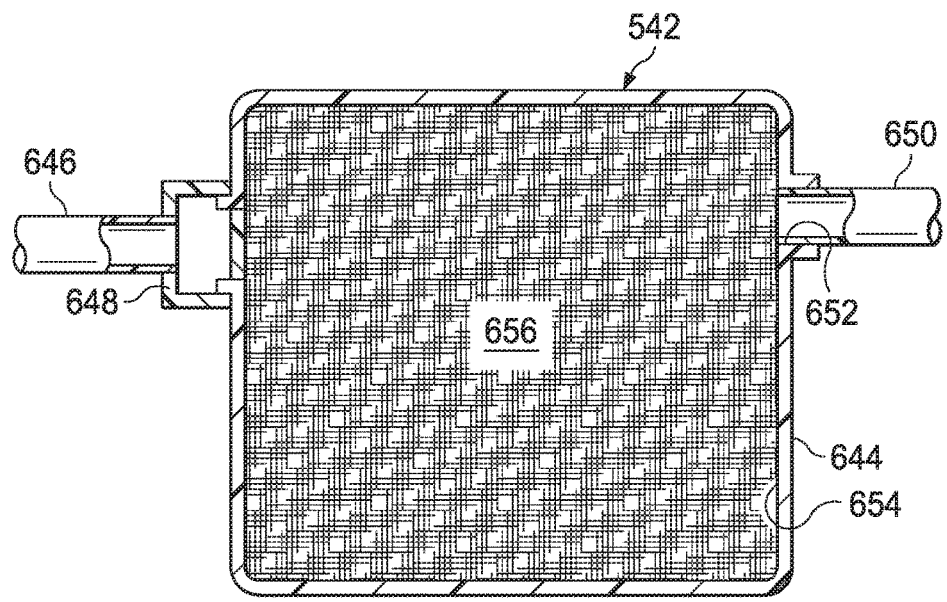
FIG. 6 is a sectional view of an illustrative embodiment of a container of the reduced-pressure therapy system of FIG. 5.

FIG. 6 is a sectional view illustrating additional details that may be associated with some embodiments of the container 542. In some embodiments, the container 542 comprises a body 644 having an interior 654. In some embodiments, an absorbent sheet 656 may be disposed within the interior 654 of the container 542. The absorbent sheet 656 may include or may be formed from one or more fiber matrices, such as the fiber matrix 104, for example.

In some exemplary embodiments, the absorbent sheet 656 may substantially fill the interior 654. In other exemplary embodiments, the absorbent sheet 656 may fill only a portion of the interior 654. The interior 654 of the container 542 may be adapted to allow for the absorbent sheet 656 to expand if the absorbent sheet 656 absorbs fluid from a tissue site. In some embodiments, the container 542 may be rigid, and the absorbent sheet 656 may not substantially fill the interior 654, leaving space for expansion of the absorbent sheet 656. In some embodiments, the container 542 may be flexible, and the interior 654 may be configured to expand to accommodate expansion of the absorbent sheet 656. In addition, the amount and disposition of the absorbent sheet 656 within the interior 654 may vary as needed to allow fluid communication of reduced pressure through the container 542 to the dressing 532.

The container 542 may further include a fluid inlet 648 and a fluid outlet 652. In some embodiments, the fluid inlet 648 may pass through a wall of the container 542 to provide fluid communication between the interior 654 and an area outside of the container 542. In some embodiments, a tube 646 may fluidly couple to the fluid inlet 648 so that the tube 646 may provide fluid communication between the dressing 532 and the interior 654. The fluid outlet 652 may extend through a wall of the container 542 to provide fluid communication between the body interior 654 and an area outside of the container 112. In some embodiments, a tube 650 may be fluidly coupled to the fluid outlet 652 and may be further fluidly coupled to a reduced-pressure source, such as the reduced-pressure source 534, allowing for fluid communication between the reduced-pressure source and the interior 654. The fluid inlet 648 and the fluid outlet 652 may be positioned on the container 542 as shown in FIG. 6. In other embodiments, the fluid inlet 648 and the fluid outlet 652 may be positioned in other locations to accommodate additional components of the reduced-pressure therapy system 500. For example, the container 542 may be combined with a reduced-pressure source. In this example, the fluid inlet 648 and the fluid outlet 652 may be disposed on other portions of the container 542 to accommodate the positioning of various components of the combined container 542 and a reduced-pressure source.

In operation, the reduced-pressure source 534 may supply reduced pressure to the dressing 532, including the manifold 540, and ultimately a tissue site. The reduced pressure may draw fluids out of the tissue site, and the manifold 540 may distribute the fluids from the tissue site to the dressing 532. The fluids drawn from the tissue site may have a high ionic concentration. Upon reaching the dressing 532, the fluids may come into contact with the absorbent layer 502, which may include fibers with ion-exchange media, such as the fiber 106, the fiber 306, or the fiber 420. If wound fluid comes into contact with the fibers 106, for example, the ion-exchange media 212 in the filter layer 210 can exchange salt ions, such as sodium and chloride ions, with the fluid. The ionic salt content of the fluid may be removed or substantially reduced before contacting the core 208, thus enabling the core 208 to absorb a significantly higher amount of fluid.

In some embodiments, while much of the fluid drawn from a tissue site may be absorbed by the absorbent layer 502, some fluid may be drawn through the dressing 532. In other embodiments, the dressing 532 may not include the absorbent layer 502, or the absorbent layer 502 may not include ion-exchange media. Fluid not retained by the dressing 532 may be drawn to the container 542, and into the interior 654 of the container 542. Fluid drawn into the interior 654 may come into contact with the absorbent sheet 656 in the interior 654 of the container 542. The absorbent sheet 656 may include absorbent fibers with an ion-exchange fiber, as described above. An ion-exchange fiber can reduce the ionic concentration of fluid, as described above, before fluid is absorbed by the core of the absorbent fibers. Fluid passing into the core may have a reduced ionic concentration, allowing for increased absorption efficiency by the absorbent sheet 656, which can also increase the capacity of the container 542.

The systems, apparatuses, and methods described herein may provide significant advantages, some of which have already been mentioned. For example, an ion-exchange fiber can significantly increase the absorbent capacity of an absorbent fiber. The increased absorbent capacity may allow the amount of absorbent used in a dressing or container to be reduced, enabling a smaller dressing or container to be used, for example. In addition, using less absorbent material can provide a potential cost savings. For example, reducing use of SAP may decrease the cost to produce the absorbent and decrease the cost of other materials, such as drapes or wicking layers, for example. The gram-for-gram fluid management capacity of a dressing can be improved without relying on other factors such as evaporation.

Additionally, an ion-exchange fiber with a super-absorbent may be advantageous for producing a low profile dressing. For example, by combining a super-absorbent core and IEM together in the manner described above, the net efficiency of an absorbent dressing may be significantly improved. In some instances, for example, the net efficiency can be increased by approximately 25%, whether or not the dressing is under compression. Furthermore, by disposing a water-permeable layer including TEM around a super-absorbent core, structural integrity can be added to the absorbent structure, which can prevent the structure from becoming dissociated when at full absorptive capacity or during dressing changes. Similarly, by binding an IEM to an absorbent fiber, the chances of the IEM being free or mobile are reduced.

While some exemplary embodiments are described in the context of reduced-pressure therapy applications, many of the features and advantages are readily applicable to other environments and industries.

Although certain illustrative, non-limiting exemplary embodiments have been presented, various changes, substitutions, permutations, and alterations can be made without departing from the scope of the appended claims. Any feature described in connection to any one exemplary embodiment may also be applicable to any other exemplary embodiment.

Further, the steps of the methods described herein may be carried out in any suitable order, or simultaneously where appropriate.

What is claimed is:

1. A fiber, comprising:
an absorbent core; and
a filter layer surrounding the absorbent core and comprising an ion-exchange media adapted to reduce an ionic concentration of a fluid prior to the fluid coming into contact with the absorbent core;
wherein the ion-exchange media comprises cation-exchange media and anion-exchange media that are dispersed throughout the filter layer.

2. The fiber of claim 1, wherein the filter layer is coated on the absorbent core.

3. The fiber of claim 1, wherein the filter layer encloses the absorbent core.

4. The fiber of claim 1, wherein the ion-exchange media comprises porous beads formed from cross-linked polymers doped or grafted with acidic polymers.

5. The fiber of claim 4, wherein the cross-linked polymers comprise polystyrene and the acidic polymers comprise poly (2-acrylamido-2-methyl-1-propanesulfonic acid) and poly (acrylamido-N-propyltrimethylammonium chloride).

6. The fiber of claim 1, wherein the ion-exchange media comprises an alkaline polymer.

7. The fiber of claim 6, wherein the alkaline polymer is poly(acrylamido-N-propyltrimethylammonium chloride).

8. The fiber of claim 1, wherein the ion-exchange media comprises a zeolite.

9. The fiber of claim 1, wherein the filter layer is water-permeable.

10. The fiber of claim 1, wherein the filter layer comprises a polymer coating.

11. The fiber of claim 10, wherein the polymer coating comprises at least one of cross-linked polyvinyl alcohol, polyvinyl pyrrolidone, polyurethane, polyacrylamide, and polyethylene oxide.

12. The fiber of claim 1, wherein the absorbent core comprises a super-absorbent material.

13. The fiber of claim 12, wherein the super-absorbent material is a super-absorbent polymer.

14. The fiber of claim 13, wherein the super-absorbent polymer is a hydrogel.

15. An absorbent dressing, comprising:
   an ion-exchange media adapted to reduce an ionic concentration of a fluid; and
   an absorbent surrounded by the ion-exchange media, such that the ionic concentration of the fluid is reduced prior to the fluid coming into contact with the absorbent, and wherein the absorbent is adapted to absorb fluid with the reduced ionic concentration;
   wherein the absorbent comprises an absorbent strand and the ion-exchange media is dispersed in strands twisted around the absorbent strand.

16. The absorbent dressing of claim 15, wherein the absorbent is formed into a plurality of absorbent fibers.

17. The absorbent dressing of claim 15, wherein the ion-exchange media comprises a cation-exchange media.

18. The absorbent dressing of claim 15, wherein the ion-exchange media comprises an anion-exchange media.

19. The absorbent dressing of claim 15, wherein the ion-exchange media is dispersed in a filter layer around the absorbent.

20. The absorbent dressing of claim 15, wherein the absorbent comprises a super-absorbent material.

21. The absorbent dressing of claim 20, wherein the super-absorbent material is a super-absorbent polymer.

* * * * *